United States Patent
Pinney et al.

(10) Patent No.: US 6,358,060 B2
(45) Date of Patent: *Mar. 19, 2002

(54) TWO-STAGE TRANSMUCOSAL MEDICINE DELIVERY SYSTEM FOR SYMPTOM RELIEF

(75) Inventors: John M. Pinney, Bethesda; Jack E. Henningfield, Baltimore, both of MD (US); Saul Shiffman, Pittsburgh, PA (US); Joseph Gitchell, Bethesda; Edward J. Cone, Severna Park, both of MD (US)

(73) Assignee: JSR LLC, Bethesda, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/146,696

(22) Filed: Sep. 3, 1998

(51) Int. Cl.[7] ............... A61F 13/02; A01N 43/40
(52) U.S. Cl. ............... 434/435; 424/434; 424/449; 514/343; 514/813
(58) Field of Search ............... 424/434, 435, 424/449; 514/343, 813

(56) References Cited

U.S. PATENT DOCUMENTS

| 1,038,227 A | 9/1912 | Sulzberger |
| 2,262,087 A | 11/1941 | Bartlett ............... 167/82 |
| 2,536,168 A | 1/1951 | Goggin ............... 167/82 |
| 3,845,217 A | 10/1974 | Ferno et al. ............... 426/3 |

(List continued on next page.)

FOREIGN PATENT DOCUMENTS

| CA | 2109895 | 5/1995 | |
| GB | 2 255892 | 11/1992 | |
| GB | 2299756 | 10/1996 | |
| WO | 9320821 | 10/1993 | ......... A61K/31/495 |
| WO | 9512399 | 5/1995 | ......... A61R/31/465 |
| WO | 9710162 | 3/1997 | ......... B65D/85/72 |
| WO | WO 97/42941 | 5/1997 | |
| WO | 9741858 | 11/1997 | ......... A61K/31/495 |

OTHER PUBLICATIONS

Henningfield et al, Drinking Coffee and Carbonated Beverages Blocks Absorption of Nicotine From Nicotine Polacrilex Gum, Sep. 26, 1990, pp. 1560–1564, The Journal of the American Medical Association.

Henningfield et al, Nicotine Dependence Interface vbetween Tobacco and Tobacco–related disease, Feb. 1988, pp. 37–53, CHEST.

(List continued on next page.)

Primary Examiner—Thurman K. Page
Assistant Examiner—R. Joynes
(74) Attorney, Agent, or Firm—Liniak, Berenato, Longacre & White, LLC

(57) ABSTRACT

A two-stage medicine delivery system provides an initial dose of medicine and a second dose of medicine. The initial second doses are capable of achieving a rapid pharmacological effect and a prolonged pharmacological effect, respectively. The two-stage medicine delivery system preferably delivers a craving reduction substance, in which case, the rapid and prolonged pharmacological effects include a rapid and prolonged craving reduction. Preferably, the delivery system is a nicotine delivery system which is provided in chewing gum form or lozenge form and which provides the nicotine in a transmucosally absorbable form. The two-stage medicine delivery system preferably releases a buffering agent which increases a pH level in a user's mouth to facilitate absorption of the medicine when the delivery system is placed in the user's mouth. A method of making the medicine delivery system also is provided. The system and apparatus can be adapted to reduce cravings for alcohol, food, drugs (e.g., cocaine, opiates and the like) and tobacco products, especially tobacco products containing nicotine.

74 Claims, 3 Drawing Sheets

U.S. PATENT DOCUMENTS

| | | | |
|---|---|---|---|
| 3,877,468 A | 4/1975 | Lichtneckert et al. | 131/2 |
| 3,901,248 A | 8/1975 | Lichtneckert et al. | 131/2 |
| 3,984,574 A | 10/1976 | Comollo | 426/4 |
| 4,139,589 A | 2/1979 | Beringer et al. | 264/250 |
| 4,163,777 A | 8/1979 | Mitra | 424/21 |
| 4,238,475 A | 12/1980 | Witzel et al. | 424/48 |
| 4,276,890 A | 7/1981 | Fichera | 131/270 |
| 4,311,691 A | 1/1982 | Fichera | 424/48 |
| 4,515,769 A | 5/1985 | Merritt et al. | 424/49 |
| 4,620,982 A | 11/1986 | Serpelloni | 426/658 |
| 4,639,368 A | 1/1987 | Niazi et al. | 424/48 |
| 4,671,953 A | 6/1987 | Stanley et al. | 424/440 |
| 4,711,784 A | 12/1987 | Yang | 426/5 |
| 4,806,356 A | 2/1989 | Shaw | 424/440 |
| 4,832,994 A | 5/1989 | Fey | 428/48 |
| 4,855,326 A | 8/1989 | Fuisz | 514/777 |
| 4,863,737 A | 9/1989 | Stanley et al. | 424/440 |
| 4,907,605 A | 3/1990 | Ray et al. | 131/270 |
| 4,963,369 A | 10/1990 | Song et al. | 426/5 |
| 4,967,773 A | 11/1990 | Shaw | 131/359 |
| 4,971,079 A | 11/1990 | Talapin et al. | 131/359 |
| 4,971,806 A | 11/1990 | Cherukuri et al. | 426/5 |
| 4,983,378 A | 1/1991 | Parnell | 424/48 |
| 4,985,252 A | 1/1991 | Jung et al. | 424/439 |
| 5,069,904 A | 12/1991 | Masterson | 424/401 |
| 5,122,127 A | 6/1992 | Stanley | 604/890.1 |
| 5,132,114 A | 7/1992 | Stanley et al. | 424/440 |
| 5,135,753 A * | 8/1992 | Baker et al. | 424/435 |
| 5,139,787 A | 8/1992 | Broderick et al. | 424/486 |
| 5,147,648 A | 9/1992 | Bannert | 424/435 |
| 5,147,654 A | 9/1992 | Place et al. | 424/473 |
| 5,154,927 A | 10/1992 | Song et al. | 424/440 |
| 5,154,939 A | 10/1992 | Broderick et al. | 426/5 |
| 5,158,772 A | 10/1992 | Davis | 424/401 |
| 5,198,251 A | 3/1993 | Song et al. | 426/5 |
| 5,244,668 A | 9/1993 | Snipes | 424/435 |
| 5,288,497 A | 2/1994 | Stanley et al. | 424/440 |
| 5,288,498 A | 2/1994 | Stanley et al. | 424/440 |
| 5,302,394 A | 4/1994 | Beahm | 424/440 |
| 5,312,626 A | 5/1994 | Gergely et al. | 424/441 |
| 5,334,390 A | 8/1994 | Solomon et al. | 424/439 |
| 5,362,496 A | 11/1994 | Baker et al. | 424/435 |
| 5,364,627 A | 11/1994 | Song | 424/443 |
| 5,380,535 A | 1/1995 | Geyer et al. | 424/484 |
| 5,399,354 A | 3/1995 | Ells et al. | 424/440 |
| 5,437,872 A | 8/1995 | Lee | 424/464 |
| 5,462,754 A | 10/1995 | Synosky et al. | 426/4 |
| 5,487,902 A | 1/1996 | Anderson et al. | 426/3 |
| 5,488,962 A | 2/1996 | Perfetti | 131/270 |
| 5,525,351 A | 6/1996 | Dam | 424/440 |
| 5,543,424 A | 8/1996 | Carlsson et al. | 514/343 |
| 5,549,906 A | 8/1996 | Santus | 424/440 |
| 5,593,684 A | 1/1997 | Baker et al. | 424/435 |
| 5,599,554 A | 2/1997 | Majeti | 424/448 |
| 5,662,920 A | 9/1997 | Santus | 424/435 |
| 5,711,961 A | 1/1998 | Reiner et al. | 424/441 |
| 5,721,257 A | 2/1998 | Baker et al. | 514/343 |
| 5,783,207 A | 7/1998 | Stanley et al. | 424/440 |
| 5,785,989 A | 7/1998 | Stanley et al. | 424/440 |
| 5,834,002 A | 11/1998 | Athanikar | 424/440 |
| 5,855,908 A | 1/1999 | Stanley et al. | 424/440 |
| 5,908,614 A | 6/1999 | Montgomery | 424/53 |
| 5,912,007 A | 6/1999 | Pan et al. | 424/440 |
| 5,935,604 A | 8/1999 | Illum | 424/501 |
| 5,955,098 A | 9/1999 | Dugger, III | 424/435 |
| 5,955,099 A | 9/1999 | White | 424/440 |
| 5,955,107 A | 9/1999 | Augello et al. | 424/465 |

OTHER PUBLICATIONS

Nemeth–Coslett et al, Nicotine Gum: Chew Rate, Subjective Effects and Plasma Nicotine, 1988, pp. 747–751, Pharmacology Biochemistry & Behavior, vol. 29.

Henningfield et al, Abuse Liability and Pharmacodynamic Characteristics of Intravenous and Inhaled Nicotine, 1985, pp. 1–12, The Journal of Pharmacology and Experimental Therapeutics, vol. 234, No. 1.

Nemeth–Coislett et al, Nicotine Gum: dose–related effects on cigarette smoking and subjective ratings, 1987, pp. 424–430, Psychopharmacology.

* cited by examiner

TWO-STAGE TRANSMUCOSAL MEDICINE DELIVERY SYSTEM FOR SYMPTOM RELIEF

BACKGROUND OF THE INVENTION

The present invention relates to a two-stage medicine delivery system and method for making the two-stage medicine delivery system, wherein an initial dose of medicine is capable of achieving a rapid pharmacological effect, whereas a second dose achieves a prolonged pharmacological effect. The invention also is directed to an improved methodology for symptom relief, such as relief from cravings attributable to withdrawal (e.g., nicotine withdrawal).

The term "medicine", as used herein, is not limited to substances which relieve pain, disease and/or infection. To the contrary, the term "medicine" encompasses virtually any therapeutic substance which can be effectively applied using the system of the present invention to achieve some desired result. Similarly, the term "lozenge" as used herein is not limited to products that are hard and have a flat, diamond-like shape, but rather encompasses any candy-like source of a therapeutic substance irrespective of its shape, such as gum. The term "lozenge" includes those substitutes by which medicine may be transmucosally delivered to the user.

Most conventional medicine delivery systems have limitations which make them less than ideal. One limitation relates to the speed of delivery. Few medicine delivery systems can provide a pharmacological effect within five minutes of use, much less within one to three minutes of use, and then provide sustainable (or on-demand) delivery for over 30 minutes. The delay in pharmacological effect is especially problematic in situations where the patient takes the medication in response to a stimulus. Examples of such situations include patients who take the medication in response to heart palpitations, diabetics who take the medication in response to noticeable glucose variations, addicts who take craving-reduction medicine in response to cravings, patients who take medication in response to panic attacks, and those seeking to stop smoking and experiencing a craving for a cigarette. In those patients, dangerous complications could arise if the medication is delivered ineffectually or at too fast of a rate.

Another limitation relates to variations in concentration of medicine achieved in the user's bloodstream. Few, if any, medicine delivery systems can provide substantially constant concentrations of medicine in the bloodstream. It is desirable, however, to provide a substantially constant concentration which remains at or near the level of pharmacological effect (LPE). Concentrations below the LPE may have little, if any, effect on the symptoms which the patient wishes to alleviate. Thus, when a medicine delivery system provides such low concentration, it is doing little, if anything, to alleviate the patient. Similarly, concentrations of medicine above the LPE typically are unnecessary, and can produce side-effects or reactions to the medication. There is consequently a need for a medicine delivery system which provides an initial dose of medicine sufficient to rapidly achieve a medicine concentration in the user's bloodstream at or near the LPE and which thereafter provides another more prolonged dose capable of maintaining the concentration of medicine in the user's bloodstream substantially constant at or near the LPE.

Conventional oral delivery systems fail to provide the foregoing combination of doses and the desirable results associated therewith. Typically, the conventional oral delivery system has a delay of 1–3 hours before reaching the LPE. Thereafter, it is unable to maintain a substantially constant concentration at or near the LPE. Instead, the desired pharmacological effect is achieved over a period of time by exceeding the concentration associated with the LPE, followed by a rapid decline in concentration below the LPE.

A typical curve CC representing the concentrations achieved by such an oral delivery system is illustrated in FIG. 1. The illustrated strategy disadvantageously exposes the patient to an over-dosage, as indicated by the portion of the concentration curve CC which appears far above the LPE line. The resulting overdosage tends to produce toxic side-effects or reactions to the medication.

In addition, the concentration curve CC remains below the LPE line for a significant period of time after the medication is taken. The length of this delay may vary and is affected by the speed of ingestion. This represents a potentially unacceptable delay in the desired pharmacological effect. This delay is particularly unacceptable where the medicine is used to reduce cravings. In those situations, the delay may be long enough that the patient succumbs to the craving. Smokers, for example, might smoke before the orally taken medicine can produce a reduction in the nicotine craving.

The concentration curve CC also drops below the LPE line after the over-dosage. This likewise represents a period of time between dosages where the patient is not receiving the benefit of the desired pharmacological effect.

Although the period of time between pills can be decreased in an attempt to reduce the magnitude of the overdosages, this becomes inconvenient to the patient and greatly increases the likelihood that the patient will not comply with the dosage requirements and therefore will not receive the full benefit of the desired pharmacological effect. In order to avoid non-compliance, the medicine delivery system should minimize the amount of activity required of the patient.

An additional problem with conventional oral medicine delivery systems which require stomach absorption of the medicine is the highly volatile enzymatic environment of the gastro-intestinal system. This environment can alter the medicine and reduce or eliminate its effectiveness.

In order to provide more immediate pharmacological effects, hypodermic injection has been used as a medicine delivery system. Such injection techniques, however, fail to provide constant concentrations of the medicine in the blood over prolonged periods of time.

FIG. 2 illustrates a typical concentration curve CC' which represents the concentration of medicine in the blood over time when a conventional hypodermic injection technique is used. The concentration curve CC' demonstrates how the initial dosage actually exceeds the LPE necessary to achieve the desired pharmacological effect. The hypodermic injection technique therefore exposes the patient to an over-dosage. This over-dosage, in turn, increases the likelihood of side-effects and adverse reactions. Another disadvantage associated with the conventional hypodermic injection technique is that it fails to provide a prolonged period of time during which the concentration remains at or near the LPE. Instead, the concentration curve CC' reaches a peak soon after injection and progressively diminishes over time.

Yet another disadvantage associated with conventional hypodermic injection techniques is the pain associated with such injection techniques. Some patients are extremely disturbed by the notion of hypodermic injection. This limits the number of patients which will use the injection technique. Even the patients which do elect to use the hypodermic injection technique may be less likely to comply on a regular basis with dosage requirements when faced with the unpleasantness of frequent injections. In many cases, the injection technique requires medical personnel, privacy, and/or a stationary place to perform the injection. When all three requirements are present, the injection technique is extremely inconvenient to the patient.

Another conventional technique for delivering medicine involves an intravenous drip. The intravenous drip is capable of providing a rapid pharmacological effect and can be programmed to dispense medicine at a rate which achieves a substantially constant concentration of medicine in the blood, at or near the LPE. A typical curve CC" representing the concentrations achieved by the intravenous drip technique is illustrated in FIG. 3.

The intravenous drip, however, requires trained medical personnel to supervise the delivery of medicine. This can result in delay because medical personal usually cannot respond immediately. The requirement of medical personnel also makes the intravenous drip technique very inconvenient for the patient. Another disadvantage associated with the intravenous drip technique is the need to insert a catheter subcutaneously. The initial insertion may be painful and uncomfortable, making this technique difficult on patients. In addition, the patient's mobility may be significantly hampered during the intravenous delivery of the medicine.

The intravenous drip technique is especially difficult to implement on an effective basis when the medicine is a craving reduction medicine. In those situations, it is impractical to have the patient meet with medical personnel to have a catheter inserted every time the patient experiences a craving.

Inhalation techniques also have been used to deliver medicine. Although such techniques may provide rapid and effective pharmacological effects, it is difficult to regulate the concentration of medicine in the blood over a prolonged period of time when such techniques are used.

Another conventional technique for delivering medicine involves the use of chewing gum. The chewing gum includes a medicine which is released into the mouth when the gum is chewed. Such gums can provide a relatively constant concentration of medicine, with slight variations from that consentration, in the chewer's blood. Accordingly, the LPE can be achieved using concentrations which do not deviate much higher than the LPE and do not vary significantly from the LPE. The chewing gum-based technique therefore advantageously avoids the over-dosage problems associated with conventional, orally administered medications which are not chewed but are immediately swallowed. A typical curve CC'" representing the concentrations achieved by the chewing gum-based delivery systems is illustrated in FIG. 4.

A disadvantage associated with conventional gum chewing techniques, however, is the delay between the time when chewing begins and onset of the desired pharmacological effect. The delay typically is caused by the time it takes for sufficient medicine to be released from the gum and for that medicine to be absorbed into the bloodstream.

In the case of gums which are used to counteract cravings for nicotine-containing products, a substantial portion of the nicotine from such gums may be swallowed because of poor absorption in the mouth. Since nicotine, when swallowed, can cause adverse gastrointestinal symptoms, such as hiccupping and nausea, the conventional chewing gum technique can produce undesirable side-effects.

If the gum fails to provide a desired level of craving relief, attempts to obtain additional nicotine from the gum may cause increased feelings of nausea because of the frequent failure of users to absorb (rather than swallow) the nicotine. Thus, the effectiveness of conventional nicotine delivery gums may be difficult to adjust upwardly without experiencing an increased potential for nausea.

Despite the disadvantages associated with conventional nicotine delivering gum, there are commercially available versions of the gum, one of which is marketed using the trademark Nicorette™. Although the sensory effects of Nicorette™ provide an initial level of craving relief which is comparable to that which is produced by confectionery chewing gum, it is the delivery of nicotine to the bloodstream which produces objectively documented effects of craving relief. The delivery of nicotine to the bloodstream generally provides discriminable effects to the user (e.g., "feel the drug"), reduced desire for smoking, restoration of cognitive performance, and reversal of withdrawal-associated EEG disruption. See e.g., Henningfield et al., Pathophysiology of Tobacco Dependence, (1995), which appears in Bloom & Kupfer, *Psychopharmacology: The Fourth Generation of Progress*, Raven Press, pp. 1715–1729; Benowitz, Pharmacology of Nicotine: Addition and Therapeutics, Annual Review of Pharmacology and Toxicology, 36: 597–613.

Studies on the effects of Nicorette™ provide a basis for determining the doses at which various effects occur. For example, the approximately one milligram of nicotine delivered over 15–30 minutes by the 2 milligram version of Nicorette™ provides detectable effects, with minimal risk of nausea and undesirable pharmacologic consequences for most users. When the dose is increased, for example by using the 4 milligram version of Nicorette™ (which delivers about 2 milligrams of nicotine) or by administering multiple units of Nicorette™ (up to 4 units of the 4 milligram version of Nicorette™), the reliability of the craving reduction increases, but the probability of undesirable consequences, such as dizziness and nausea, also increases.

An important finding from the foregoing studies is that the craving-reducing effects of nicotine on the body are almost exclusively due to the nicotine which is absorbed into the bloodstream. Nicotine which remains in the saliva and/or is swallowed has very little effect beyond its flavor-induced sensory effects and stomach upset produced by excessive amounts of swallowed nicotine.

Nicotine from Nicorette™ reaches the bloodstream in several different ways. See e.g., Benowitz & Savanapridi, Determinants of Nicotine Intake While Chewing Nicotine Polacrilex Gum, Clinical Pharmacology and Therapeutics, 41(4), pp. 467–473. About 50% of the nicotine from the 2 and 4 milligram versions of the Nicorette™ is released from the gum during chewing. The rest of the nicotine typically remains in the gum and is discarded by the user.

Of the nicotine delivered by the 2 milligram version of the Nicorette™ gum to the saliva, about 0.8 milligram is absorbed through the membranes of the mouth (the buccal mucosa) and appears in the bloodstream. The remaining approximately 0.2 milligram is swallowed, of which 0.06 milligram survives first pass hepatic metabolism and appears in the bloodstream. The 4 milligram version of Nicorette™ gum achieves nicotine absorption values which are approximately twice those of the 2 milligram version.

Although the amount of nicotine absorption from Nicorette™ is related to the chewing rate and the time the saliva is held in the mouth, these variables are significant only at the extremes of rapid chewing versus little oral action, and frequent swallowing versus infrequent swallowing. Outside of such extremes, these variables have very little impact on nicotine absorption. Thus, it takes approximately 10 to 30 minutes to achieve absorption of the nicotine from Nicorette™ into the bloodstream, regardless of whether the "park and chew" (or "chew and park") method is used or chewing at regular intervals (e.g., one chew per 4 seconds).

This initial delay, however, may be excessively long for someone who is trying to quit smoking. It is not unusual for a cigarette smoker to succumb to a nicotine craving within ten minutes of onset, especially if work or a stressful situation delays the use of the Nicorette™ beyond initial onset of the craving.

There is consequently a need for a nicotine delivery system which avoids the disadvantages associated with Nicorette™ gum (e.g., the initial delay in nicotine delivery) by providing rapid craving relief and which therefore minimizes the likelihood that a former smoker will succumb to his craving.

In providing such a nicotine delivery system, the documented effects of conventional nicotine sources, such as Nicorette™ gum, cigarettes, cigars, transdermal patches, and snuff have been considered to arrive at a delivery system which provides beneficial absorption characteristics.

Scientific data on the determinants of nicotine absorption through the membranes of the mouth, nose and epidermis, has been studied in detail since at least the 1940s. Much of this work has been reviewed in detail by the U.S. Food and Drug Administration (FDA). S. L. Tomar & J. E. Henningfield, for example, prepared a report entitled Review of the Evidence that pH is a Determinant of Nicotine Dosage from Oral use of Smokeless Tobacco, Tobacco Control, 6:219–225 (1997).

Based on the various studies, including studies of the epidermis and the buccal mucosa, the two major determinants of nicotine absorption are (1) the concentration of nicotine solution on the membrane and (2) the pH of the nicotine solution. The importance of these two determinants transcends a broad range of nicotine-containing applications, including transdermal patches, the nicotine-containing aerosol from tobacco smoke or the vapor inhaler marketed by Pharmacia, the micro environment of nicotine and moisture between the user's gum and cheek when moist snuff products are used, as well as the saliva-nicotine solution produced when Nicorette™ gum is chewed.

In the case of transdermal patches, for example, the initial form of dose control is provided by regulating the amount of nicotine which is applied against the epidermis. Once a predetermined amount of nicotine reaches the dermal membrane, the pH of the nicotine-containing solution determines the speed of absorption.

The Nicoderm™ patch, for example, carries 1–4 milligrams of nicotine in its surface layer to provide an initial burst of nicotine. The initial burst of nicotine is then followed by a controlled release from the patch reservoir. While the initial burst of nicotine is relatively rapid when compared to that provided by most other commercially available transdermal nicotine patches, it is still slow (about 30 minutes to achieve a significant increase in nicotine blood level) when compared to what can be achieved by delivery through the mouth. Dose-ranging studies were performed to determine the optimal amount of nicotine and amount and type of buffer to maximize absorption and to minimize skin irritation.

The relationship of the pH to the absorption rate of nicotine also was documented by O. Ferno in 1977, who concluded that unbuffered formulations were ineffective at nicotine delivery or relieving withdrawal symptoms. See Ferno, Development of a Chewing Gum Containing Nicotine and Some Comments on the Role Played by Nicotine in the Smoking Habit, in Steinfeld et al., Smoking & Health, Proceeding of the 3rd World Conference on Smoking and Health, Washington, D.C. (1977).

This led to the addition of 30 milligrams of sodium-based buffers to the gum formulations. The 2 milligram version of Nicorette™, for example, contains 10 milligrams of sodium bicarbonate and 20 milligrams of sodium carbonate. The 4 milligram version of Nicorette™ contains 30 milligrams of sodium carbonate.

The combination of buffers in Nicorette™ raises oral salivary pH from its typical value of about 6.9–7.3 to about 8.0 in 5–10 minutes. The act of chewing itself contributes to the rise in pH because chewing-stimulated saliva from the parotid gland contains some bicarbonate. By comparison, chewing an anti-acid tablet marketed under the trademark Tums™ (which contains calcium carbonate), produces an almost immediate increase in oral salivary pH to about 8.1.

Since Nicorette™ is physio-chemically structured so that its nicotine is evenly distributed throughout the gum, the release of nicotine depends on exposing fresh surface areas of the gum to the salivary substrate so that nicotine and buffer can be released into the saliva. The portion of nicotine which is unionized is free to be immediately absorbed through the buccal mucosa. Because the dissociation constant ($pK_a$) of nicotine is 8.0, fifty percent of the nicotine is unionized and immediately free to be absorbed when the solution is at a pH of 8.0. At this pH, residual nicotine becomes unionized as the free nicotine is absorbed. There is consequently a steady but very rapid infusion of nicotine across the membrane after the appropriate pH is reached.

There have been several practical applications of the foregoing principles which provide guidance regarding the dosing range and speed for nicotine delivery systems. At least one of the "active" Nicorette™ placebo formulations used in the 1980s and early 1990s, for example, contained 0.5 milligram of nicotine without any buffer and was a useful placebo because it produced the oral sensory effects of nicotine with minimal absorption. Unlike chewing tobacco, which is actively chewed, moist snuff is used according to instructions from the major marketers of these products in a manner that is functionally similar to the chew and park method for Nicorette™. The physical effort required to manipulate the moist snuff, however, is less than that required by Nicorette™. The instructions direct the user to place the dose between the gum and cheek, and occasionally move or otherwise orally manipulate it. When such products are used, large differences in nicotine absorption have been observed as a function of two variables, namely, nicotine concentration and pH.

The relationship between pH and absorption rate is further illustrated by the differences between cigar smoke and cigarette smoke. Cigar smoke can provide rapid delivery of nicotine when held in the mouth because cigar smoke typically has a pH in the range of 7.5 to 8.0. Cigarette smoke, by contrast, typically has a pH between 5.5 and 6.0 and therefore must be inhaled to produce effective absorption. It is believed that effective nicotine absorption does not require pH levels greater than approximately 8.5 to 9.5. Further increases above 9.5 would be expected to produce a soapy and/or burning sensation in the mouth.

A need therefore exists for a nicotine delivery system which rapidly elevates a pH level in the user's mouth so that rapid absorption of nicotine into the bloodstream can be achieved, and which also delivers nicotine over a prolonged period of time to maintain a pharmacologically appropriate concentration of nicotine in the bloodstream.

SUMMARY OF THE INVENTION

A primary object of the present invention is to overcome the foregoing disadvantages associated with conventional medicine delivery systems, by providing a convenient, reliable, practical, and relatively painless medicine delivery system.

Another object of the present invention is to provide a two-stage medicine delivery system capable of providing initial and second doses of a craving reduction medicine, the combination of which rapidly reduces such cravings and provides protection from such cravings over a prolonged period of time beyond the initial dose.

Yet another object of the present invention is to provide a two-stage nicotine delivering gum capable of providing an initial dose of nicotine which is absorbed into the bloodstream within 5 minutes after chewing begins to achieve a pharmacologically effective concentration in the bloodstream, and also capable of providing a second dose of nicotine which keeps the concentration of nicotine in the bloodstream at or near the pharmacologically effective concentration for at least 20 minutes after chewing begins.

Still another object of the present invention is to provide a two-stage medicine delivering system which is convenient to use and which does not require trained medical personnel to administer the doses or require extensive user experience to provide a rapid pharmacological effect and/or mitigation of undesirable symptoms.

Another object of the present invention is to provide a medicine delivery system which provides a desired concentration of the medicine in the bloodstream within 5 minutes and preferably within 1–2 minutes of administration.

Yet another object of the present invention is to provide a medicine delivery system which keeps the concentration of the medicine in the bloodstream at or near the level of pharmacological effect (LPE), without significant overdosages.

To achieve these and other objects, the present invention provides a two-stage medicine delivery system. The two-stage medicine delivery system comprises means for providing an initial dose of medicine and means for providing a second dose of medicine. The initial dose of medicine is capable of achieving a rapid pharmacological effect. The second dose, by contrast, is capable of achieving a prolonged pharmacological effect.

The two-stage medicine delivery system preferably delivers a craving counteracting substance, and the rapid and prolonged pharmacological effects include a rapid and prolonged reduction of a craving.

Preferably, the delivery system is a nicotine delivery system which is provided in chewing gum form or lozenge form and which provides the nicotine in a transmucosally absorbable form.

The two-stage medicine delivery system preferably includes means for releasing a buffering agent which increases a pH level in a user's mouth to facilitate absorption of the medicine when the delivery system is placed in the user's mouth.

The present invention also provides a method of making a medicine delivery system which reduces a craving when orally retained. According to the method, a base material is provided. The base material is adapted to be retained in a user's mouth. A loading compound is mixed into the base material so that the loading compound remains releasable and rapidly transmucosally absorbable to counteract a craving within 5 minutes after the base material is orally retained. In addition, a maintenance compound is mixed into the base material so that the maintenance compound remains releasable and transmucosally absorbable over a prolonged period of time to counteract the craving for at least 20 minutes after oral retention of the base material begins.

Preferably, a buffer is also mixed into the base material so that the buffer remains releasable to elevate a pH level and facilitate transmucosal absorption of the loading and maintenance compounds within the user's mouth when the base material is orally retained. The buffer preferably is a bicarbonate type of buffer adapted to elevate the pH level to 7.5 to 9.5, preferably about 9.0, within 5 minutes after the base material is orally retained. Preferably, the base material is a gum base or a lozenge.

The present invention also provides a two-stage nicotine delivering product for use in counteracting cravings for nicotine-containing tobacco products. The product comprises a base, a nicotine loading compound, and a nicotine maintenance compound. The nicotine loading compound is mixed with the base so that oral actuation of the base causes the nicotine loading compound to be released into a user's mouth for transmucosal absorption within the first 5 minutes after oral actuation begins. The nicotine maintenance compound, by contrast, is mixed with the base so that oral actuation of the base causes the nicotine maintenance compound to be released into the user's mouth for prolonged transmucosal absorption which lasts at least 20 minutes beyond the first five minutes.

As indicated above, the present invention is well-suited for applications where the medicine is delivered orally, and more specifically, where the oral delivery of the medicine is performed via buccal transmucosal absorption. The present invention is quite useful as a craving reducer and can be adapted to reduce cravings for alcohol, food, drugs (e.g., cocaine, opiates and the like) and tobacco products, especially tobacco products containing nicotine.

As a nicotine delivery system, the present invention provides an initial dose of nicotine and a second dose of nicotine, the combination of which effectively counteracts a user's craving for cigarettes and other tobacco products. The present invention therefore can be used effectively to help smokers quit or reduce smoking.

The above and other objects and advantages will become more readily apparent when reference is made to the following description taken in conjunction with the accompanying drawings.

DETAILED DESCRIPTION OF THE INVENTION

Figure 1:
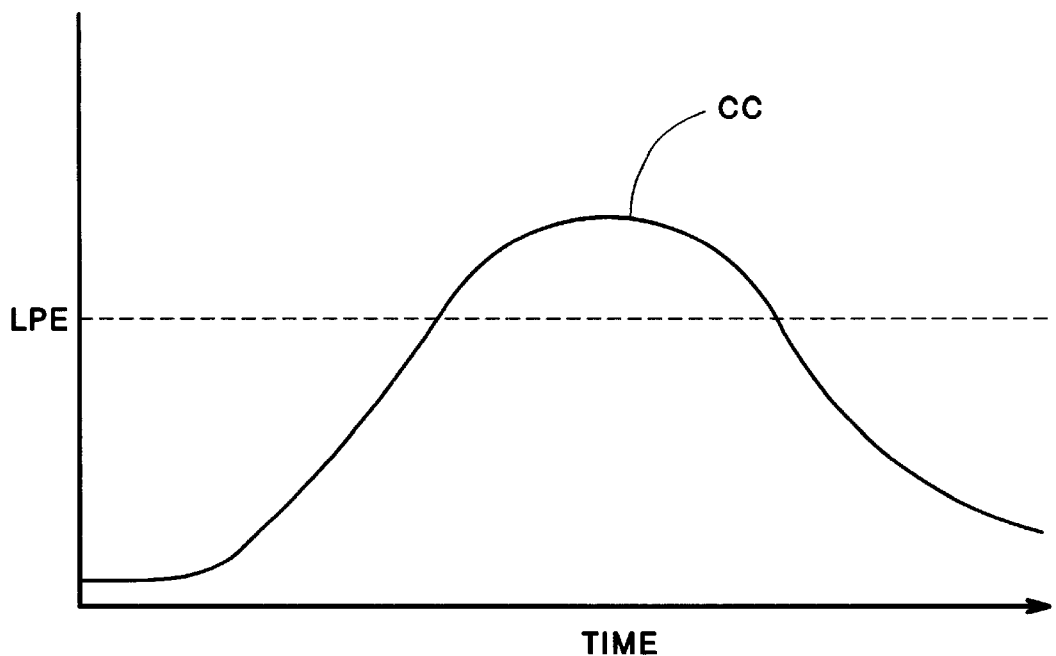
FIG. 1 is a graph illustrating medicine concentrations in the bloodstream when a conventional oral delivery system is used.
Figure 2:
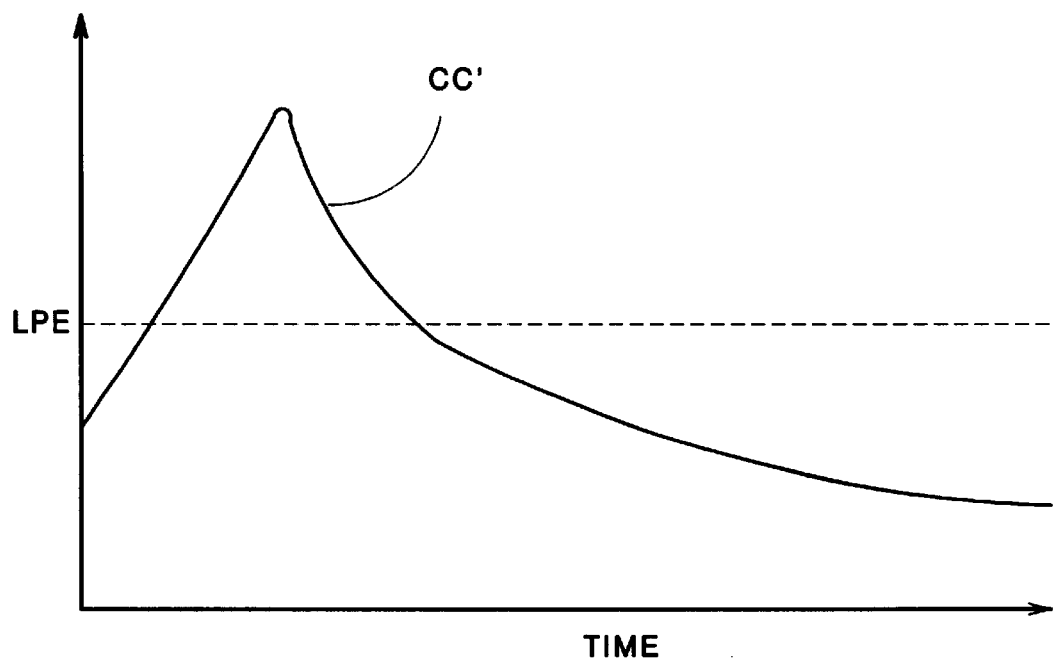
FIG. 2 is a graph illustrating medicine concentrations in the bloodstream when a conventional hypodermic injection technique is used.
Figure 3:
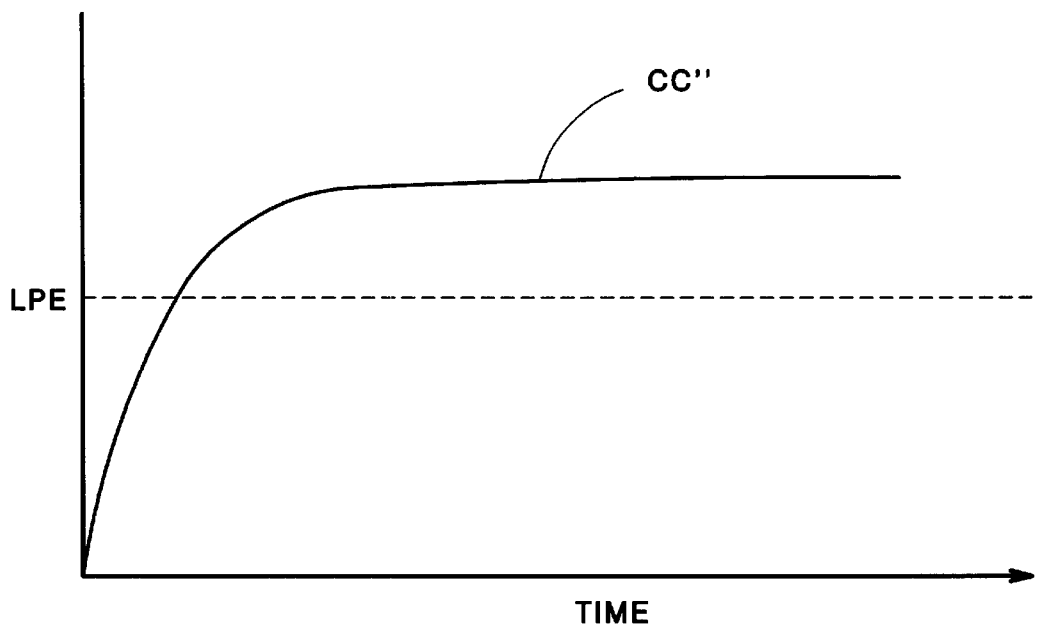
FIG. 3 is a graph illustrating medicine concentrations in the bloodstream when a conventional intravenous drip technique is used.
Figure 4:
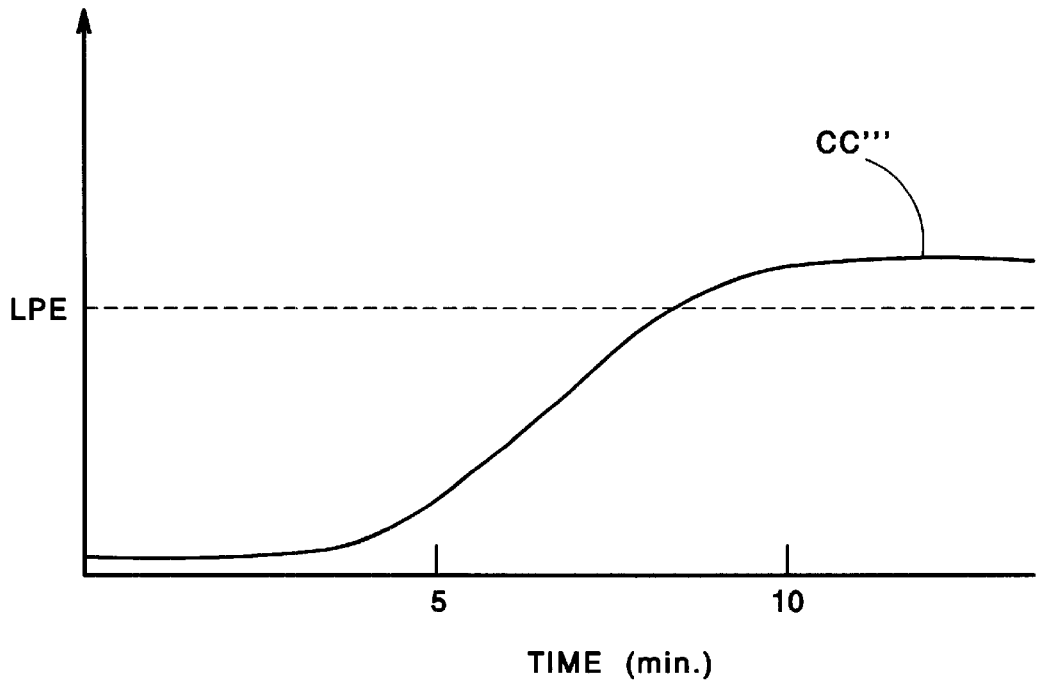
FIG. 4 is a graph illustrating medicine concentrations in the bloodstream when a conventional gum-based nicotine delivery system is used.

In order to avoid delays in medicine delivery and overdosages, the present invention provides a two-stage medicine delivery system. The two-stage medicine delivery system comprises means for providing an initial dose of medicine and means for providing a second dose of medicine. The initial and second doses are capable of achieving a rapid pharmacological effect and a prolonged pharmacological effect, respectively.

Preferably, the two-stage medicine delivery system delivers a craving counteracting substance, and the rapid and prolonged pharmacological effects provided by the system include a rapid and prolonged reduction in craving, respectively.

A preferred embodiment of the medicine delivery system is nicotine gum which delivers nicotine when chewed and which can be used to counteract cravings for nicotine-containing tobacco products. Although the nicotine gum form of the invention is preferred, it is understood that similar delivery systems may be provided in lozenge or other forms. Moreover, while the invention is preferably practiced in a manner relieving smoking withdrawal cravings, it has utility with other cravings, such as those related to eating disorders, stress, and the like, through suitable substitutions with the appropriate medicines.

The nicotine gum according to the preferred embodiment delivers the nicotine in a transmucosally absorbable form. The gum comprises a gum base, a nicotine loading compound, and a nicotine maintenance compound. The gum base can be implemented using one or a combination of several commercially available gum bases, some of which are commercially available from Fuisz Technologies. Preferably, the nicotine loading compound and/or the nicotine maintenance compound are substantially evenly distributed throughout the gum base so that distortion of the gum base's shape during chewing or oral manipulation does not significantly affect the amount and/or rate of nicotine release. In this regard, the gum base preferably does not include layers of different nicotine concentrations arranged to release different amounts of nicotine based on which layer of the gum is exposed.

The nicotine loading compound is mixed with the gum base so that chewing of the gum base causes the nicotine loading compound to be released into a chewer's mouth for transmucosal absorption within the first 5 minutes, and preferably within less than 3 minutes, after chewing begins. Preferably, the initial dose provided by the nicotine loading compound is between 0.2 and 0.7 milligram of nicotine. This initial dose is absorbed into the bloodstream within 5 minutes, and preferably within less than 3 minutes, after having been placed in the user's mouth. As a result, a loaded nicotine concentration in the bloodstream of 2 to 7 nanograms of nicotine per milliliter of blood (which is sufficient to provide craving relief) is achieved within about 5 minutes. Such a short delay in craving relief is acceptable to most former smokers and will not cause them to succumb to their cravings.

The nicotine maintenance compound, by contrast, is mixed with the gum base so that occasional chewing of the gum base causes the nicotine maintenance compound to be released into the chewer's mouth for prolonged transmucosal absorption which lasts at least 20 minutes beyond the first five minutes of use. The second dose provided by the nicotine maintenance compound is adapted to achieve a prolonged concentration of nicotine in the user's blood which is at least as high as a loaded nicotine concentration achieved in the user's blood by the initial dose.

Preferably, the nicotine maintenance compound is selected so that the prolonged concentration of nicotine is at least 10 nanograms per milliliter of blood and so that this prolonged nicotine concentration is maintained for at least 20 minutes and preferably 35 minutes after use begins.

Figure 5:
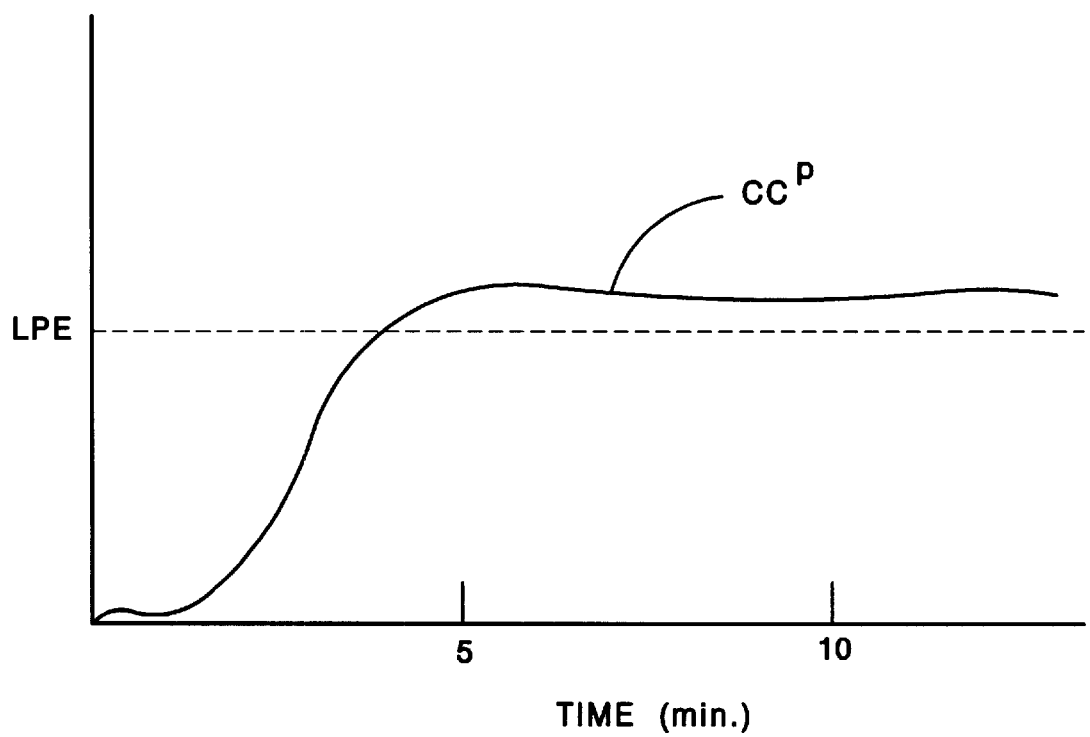
FIG. 5 is a graph illustrating concentrations of medicine which are achieved in the bloodstream when a preferred medicine delivery system according to the present invention is used.

The preferred nicotine delivering gum of the present invention achieves concentrations of nicotine in the bloodstream which, over time, substantially obey the concentration curve $CC^p$ illustrated in FIG. 5. Notably, the concentration curve $CC^p$ rises within 5 minutes after chewing begins and continues to rise to a level at or near the level of pharmacologic effect (LPE). Thereafter, the concentration curve $CC^p$ remains at or near the level of pharmacologic effect for at least 20 minutes, and preferably 35 minutes. The concentration curve $CC^p$ of the present invention advantageously does not exceed the LPE to such an extent that the user is exposed to an overdosage of nicotine.

In order to facilitate rapid craving relief, the nicotine gum of the preferred embodiment includes a releasable buffering agent which increases the pH level in the user's mouth prior to or along with release of the nicotine so that when nicotine is released into the saliva, it will be rapidly absorbed. The increased pH level thus enables rapid transmucosal absorption of the nicotine loading compound, as well as transmucosal absorption of the nicotine maintenance compound. Preferably, the buffering agent is adapted to elevate the pH level in the user's mouth to between about 7.5 and 9.5, preferably about 9.0, within 5 minutes of having been placed in the user's mouth.

Preferably, the nicotine loading compound is 0.2 to 0.7 milligram of nicotine salt, such as nicotine tartrate, which is mixed into the gum base. A preferred nicotine loading compound is 0.7 milligram of nicotine hydrogen tartrate.

The nicotine maintenance compound preferably consists of 1 to 4 milligrams of nicotine that may be held in an ion exchange resin gum, such as nicotine polacrilex. Alternatively, the nicotine maintenance compound can be provided using 1 to 4 milligrams of encapsulated nicotine salt. An exemplary nicotine maintenance compound is 1.5 milligrams of nicotine polacrilex, which in conjunction with the aforementioned preferred nicotine loading compound, achieves a total nicotine content of 2.2 milligrams of nicotine.

Preferably, the amount of buffering agent is 30 to 70 milligrams. A bicarbonate buffer may be used as the buffering agent. The type and amount of bicarbonate buffer preferably is selected to raise the pH level in the user's mouth to between about 7.5 and 9.5, preferably about 9.0, within 1 to 5 minutes after chewing begins and to maintain that pH level for about 15–30 minutes (i.e., the approximate range of time during which the gum will remain in the mouth). Preferably, the bicarbonate buffer is a sodium-free bicarbonate buffer. Alternatively, the buffer may be a carbonate buffer, which preferably is sodium-free. Calcium carbonate, for example, would be an appropriate sodium-free carbonate. Other examples of buffers which can be used include potasium citrate and dipotasium phosphate.

A buffer combination for the first dosage of sodium bicarbonate and sodium carbonate advantageously provides favorable mouth-feel and taste, and in this regard, may be preferred over other buffers. This buffer combination preferably is achieved using 20 milligrams of sodium bicarbonate and 10 milligrams of encapsulated sodium carbonate.

When the foregoing ingredients are combined, the resulting gum achieves a loaded nicotine concentration in the bloodstream of 2 to 7 nanograms per milliliter of blood within 5 minutes after use begins (stage 1) and eventually achieves a maintenance concentration of nicotine in the bloodstream of at least 5 nanograms of nicotine per milliliter of blood for an additional 20 to 35 minutes (stage 2). Notably, the gum sustains release of the nicotine in addition to providing a rapid initial release and absorption of the nicotine. This represents a significant advance over conventional gums, which generally provide a sustainable release without providing rapid release and absorption.

The rapid absorption of nicotine provided by the present invention provides additional advantages. Some research indicates that, even if the same total amount of nicotine is delivered, the psychoactive effects of nicotine on craving relief are enhanced when the rate of absorption increases. Thus, the present invention's ability to provide a prompt and rapid rise in the concentration of nicotine in the blood makes the present invention a significantly more effective craving reducer.

Advantageously, the present invention provides the rapid rise in absorption without replicating the explosive bolus associated with nasal nicotine sprays. Such sprays typically deliver 1 milligram of nicotine to the bloodstream, but pose a more significant risk of abuse and addiction. The present invention more effectively avoids such risks by employing transmucosal absorption, as opposed to the more rapid nasal absorption.

The present invention also provides the desired first and second doses regardless of whether the gum is chewed at regular intervals or is manipulated using the "park and chew" (or "chew and park") method.

The present invention also provides a method of making a medicine delivery system, and more specifically, a medicine delivery system which reduces a craving when orally retained. According to the method, a base material is provided. The base material is adapted to be retained in a user's mouth. A loading compound is mixed into the base material so that the loading compound remains releasable and rapidly transmucosally absorbable to counteract a craving within 5 minutes after the base material is orally retained. In addition, a maintenance compound is mixed into the base material so that the maintenance compound remains releasable and transmucosally absorbable over a prolonged period of time to counteract the craving for at least 20 minutes after the base material is placed in the mouth.

A buffer preferably is mixed into the base material so that the buffer remains releasable to elevate a pH level and facilitate transmucosal absorption of the loading and maintenance compounds within the user's mouth when the base material is orally retained. The buffer preferably is a bicarbonate buffer adapted to elevate the pH level to about 7.5 to 9.5 (preferably, about 9.0) within 5 minutes after the base material is orally retained. Preferably, the base material is a gum base, and the loading and maintenance compounds are therapeutic substances which counteract a user's cravings.

According to a preferred application of the method, the therapeutic substance is nicotine and the exemplary nicotine loading and maintenance compounds described above are used as the loading and maintenance compounds of the method. In addition, the exemplary buffering agent described above can be used as the buffering agent described in connection with the method.

The present invention, as indicated above, is well-suited for applications where the medicine is delivered orally, and more specifically, where the oral delivery of the medicine is performed via transmucosal absorption. The present invention is quite useful as a craving reducer and can be adapted to reduce cravings for alcohol, food, drugs (e.g., cocaine, opiates, and the like), and tobacco products, especially tobacco products containing nicotine.

The present invention also may include flavorants which are added to the base and which provide flavor, such as mint flavor, upon oral actuation. Spearmint oil or other types of mint flavor, sorbitol, xylitol, and the like are examples of the types of flavorants which can be added to the present invention. Other flavorants will become readily apparent to those of ordinary skill in the art upon reading the instant disclosure.

As an oral nicotine delivery system, the present invention provides an initial dose of nicotine and a second dose of nicotine, the combination of which effectively counteracts a user's craving for cigarettes and other tobacco products. The present invention therefore can be used effectively to help former smokers avoid smoking.

While the preferred ranges of nicotine concentrations and amounts of nicotine have been described above, it is understood that the invention is not limited to such concentrations and amounts. To the contrary, the concentrations and amounts can be adjusted depending on the target population. Some target populations require more nicotine than others. For example, smokers in Mexico generally tend to require less nicotine than many other population groups to achieve the same amount of craving relief. Heavy smokers versus light smokers also will have different nicotine requirements in general. Other factors which may affect the nicotine concentrations and amounts for different target populations include environmental, geographic, and biological differences between the target populations. Thus, it is well within the scope and spirit of the present invention to adjust the concentrations and amounts of nicotine accordingly.

In addition, the medicine need not be released in separate loading and maintenance dosages but rather can be releasable from the gum in a single initial form or manner which remains in the mouth or is reabsorbed and re-released by the base material during oral manipulation. In such an arrangement, the maintenance dosage is provided to the bloodstream by appropriately releasing a maintenance dose of buffer over the prolonged period of time, thereby facilitating the desired rate of transmucosal absorption over the maintenance period.

While this invention has been described as having a preferred embodiment, it is understood that the invention is not limited to the illustrated and described features. To the contrary, the invention is capable of further modifications, usages, and/or adaptations following the general principals of the invention and therefore includes such departures from the present disclosure as come within known or customary practice in the art to which the invention pertains, and as may be applied to the central features set forth above, and which fall within the scope of the appended claims.

We claim:

1. A two-stage medicine delivery system, comprising:
    a gum, means cooperating with said gum for providing an initial dose of a medicine capable of achieving a rapid transmucosally absorbable pharmacological effect upon oral manipulation of said gum and a second dose of said medicine capable of achieving a prolonged transmucosally absorbable pharmacological effect upon subsequent oral manipulation of said gum, said medicine being evenly distributed throughout said gum.

2. The two-stage medicine delivery system of claim 1, wherein said initial and second doses are separate forms of said medicine.

3. The two-stage medicine delivery system of claim 1, wherein the medicine is nicotine.

4. The two-stage medicine delivery system of claim 2, wherein said medicine is nicotine.

5. The two-stage medicine delivery system of claim 4, wherein one of said doses is a nicotine salt and the other of said doses is nicotine polacrilex.

6. The two-stage medicine delivery system of claim 3, wherein said initial dose releases between 0.2 and 0.7 milligrams of nicotine within 5 minutes of having been placed in a user's mouth.

7. The two-stage medicine delivery system of claim 6, wherein said means second dose maintains, for at least 20 minutes a prolonged concentration of nicotine in the user's blood which is at least as high as the nicotine concentration achieved in the user's blood by the initial dose.

8. The two-stage medicine delivery system of claim 7, wherein the initial nicotine concentration is at least 2 nanograms of nicotine per milliliter of blood.

9. The two-stage medicine delivery system of claim 8, wherein the prolonged concentration of nicotine is at least 10 nanograms of nicotine per milliliter of blood.

10. The two-stage medicine delivery system of claim 9, further comprising means for
    a buffering agent is dispersed within said gum and increases a pH
    level in the user's mouth to facilitate transmucosal absorption of nicotine.

11. The two-stage medicine delivery system of claim 1, further comprising
    a buffering agent and means for releasing said buffering agent so that the pH level in a user's mouth is increased to facilitate absorption of said medicine when said two-stage medicine delivery system is placed in the user's mouth.

12. The two-stage medicine delivery system of claim 11, wherein said medicine is nicotine.

13. The two-stage medicine delivery system of claim 12, wherein:
    said buffering agent is adapted to elevate the pH level in the user's mouth to between about 7.5 and 9.5 within 5 minutes of having been placed in the user's mouth;
    said means for providing adapted to achieve an initial nicotine concentration in the user's blood of between 2 nanograms of nicotine per milliliter of blood and 7 nanograms of nicotine per milliliter of blood, within 5 minutes of having been placed in the user's mouth; and
    said means for providing is adapted to increase the concentration of nicotine in the user's blood beyond the initial nicotine concentration to achieve a prolonged concentration of nicotine in the user's blood of at least 10 nanograms of nicotine per milliliter of blood, and is further adapted to maintain said prolonged concentration of nicotine for at least 20 minutes.

14. The two-stage medicine delivery system of claim 1, wherein said medicine is a craving counteracting substance, and said rapid and prolonged therapeutic effects include a rapid and prolonged reduction of a craving.

15. A two-stage nicotine delivering product for use in counteracting cravings for nicotine-containing tobacco products comprising:
    a base;
    a nicotine loading compound mixed with the base so that oral actuation of the base causes the nicotine loading compound to be released into a user's mouth for transmucosal absorption within the first 5 minutes after oral actuation begins; and
    a nicotine maintenance compound mixed with the base so that oral actuation of the base causes the nicotine maintenance compound to be released into the user's mouth for prolonged transmucosal absorption which lasts at least 20 minutes beyond said first five minutes.

16. The two-stage nicotine delivering product of claim 15, wherein said nicotine loading compound is 0.2 to 0.7 milligrams of a nicotine salt.

17. The two-stage nicotine delivering product of claim 16, wherein said nicotine salt is nicotine tartrate.

18. The two-stage nicotine delivering product of claim 15, wherein said nicotine maintenance compound is 1 to 4 milligrams of nicotine in an ion exchange resin gum.

19. The two-stage nicotine delivering product of claim 18, wherein said nicotine in an ion exchange resin gum is nicotine polacrilex.

20. The two-stage nicotine delivering product of claim 15, wherein said nicotine maintenance compound is 1 to 4 milligrams of encapsulated nicotine salt.

21. The two-stage nicotine delivering product of claim 15, wherein said nicotine maintenance compound is adapted to maintain, for said at least 20 minutes, a prolonged concentration of nicotine in the user's blood which is at least as high as a loaded nicotine concentration achieved in the user's blood by said nicotine loading compound.

22. The two-stage nicotine delivering product of claim 21, wherein said loaded nicotine concentration is at least 2 nanograms of nicotine per milliliter of blood.

23. The two-stage nicotine delivering product of claim 22, wherein said prolonged concentration of nicotine is at least 10 nanograms of nicotine per milliliter of blood.

24. The two-stage nicotine delivering product of claim 23, further comprising a buffering agent mixed with the base, for raising a pH level in the user's mouth to facilitate transmucosal absorption of the nicotine loading compound and the nicotine maintenance compound.

25. The two-stage nicotine delivering product of claim 23, further comprising 30–70 milligrams of a buffering agent mixed with the base, for raising a pH level in the user's mouth to between about 7.5 and 9.5 within 5 minutes of when oral actuation begins, to facilitate transmucosal absorption of the nicotine loading compound and the nicotine maintenance compound.

26. The two-stage nicotine delivering product of claim 15, further comprising a buffering agent mixed with the base, for raising a pH level in the user's mouth to facilitate transmucosal absorption of the nicotine loading compound and the nicotine maintenance compound.

27. The two-stage nicotine delivering product of claim 26, wherein:
    said buffering agent is adapted to elevate the pH level in the user's mouth to between about 7.5 and 9.5 within 5 minutes of when oral actuation begins;
    said nicotine loading compound is adapted to achieve a nicotine loaded concentration in the user's blood between 2 nanograms of nicotine per milliliter of blood and 7 nanograms of nicotine per milliliter of blood, within 5 minutes of when oral actuation begins; and said nicotine maintenance compound is adapted to increase the concentration of nicotine in the user's blood beyond the nicotine loaded concentration to achieve a prolonged concentration of nicotine in the user's blood of at least 10 nanograms of nicotine per milli-liter of blood, and is further adapted to maintain said prolonged concentration of nicotine for at least 20 minutes.

28. A method of making a medicine delivery system which reduces a craving when orally retained, said method comprising the steps of:
providing a base material which is adapted to be retained in a user's mouth;
mixing a loading compound into the base material so that said loading compound remains releasable and rapidly transmucosally absorbable to counteract said craving within 5 minutes after the base material is orally retained; and
mixing a maintenance compound into the base material so that said maintenance compound remains releasable and transmucosally absorbable over a prolonged period of time to counteract said craving for at least 20 minutes after oral retention of the base material begins.

29. The method of claim 28, further comprising the step of:
mixing a buffer into the base material so that said buffer remains releasable to elevate a pH level and facilitate transmucosal absorption of said loading and maintenance compounds within the user's mouth when the base material is orally retained.

30. The method of claim 29, wherein said buffer is a bicarbonate buffer adapted to elevate said pH level to about 7.5 to 9.5 within 5 minutes after said base material is orally retained.

31. The method of claim 28, wherein said base material is a gum base.

32. The method of claim 28, wherein said craving is a nicotine craving and said loading compound is 0.2 to 0.7 milligrams of nicotine salt.

33. The method of claim 28, wherein said craving is a nicotine craving and said maintenance compound is 1 to 4 grams of nicotine in an ion exchange resin gum.

34. The method of claim 33, wherein said 1 to 4 grams of nicotine in an ion exchange resin gum is nicotine polacrilex.

35. The method of claim 28, wherein said craving is a nicotine craving and said maintenance compound is encapsulated nicotine salt.

36. The two-stage medicine delivery system of claim 1, further comprising:
a buffering agent dispersed throughout said gum.

37. The two-stage medicine delivery system of claim 36, wherein said buffering agent is present in sufficient amount to elevate the pH in a user's mouth to between about 7.5 and 9.5.

38. The two-stage medicine delivery system of claim 37, wherein the buffering agent is present in sufficient amount to elevate the pH in a user's mouth for at least 15 minutes.

39. The two-stage medicine delivery system of claim 36, wherein the buffering agent is selected from the group consisting of bicarbonate and carbonate buffers.

40. The two-stage medicine delivery system of claim 36, wherein said buffer is a sodium free buffer.

41. The two-stage medicine delivery system of claim 36, wherein said buffer is selected from the group consisting of calcium carbonate, potassium citrate, and dipotassium phosphate.

42. The two-stage medicine delivery system of claim 41, wherein there is about 30 to 70 milligrams of buffering agent dispersed throughout said gum.

43. A method of making a delivery system which reduces craving when orally manipulated, said method comprising the steps of:
providing a base material which is adapted to be retained in the mouth of a user and to be manipulated by the user; and
providing a craving reduction compound, the compound being rapidly transmucosally absorbable upon oral manipulation to counteract a craving within about 5 minutes after the base material is orally manipulated and the compound remains releasable and transmucosally absorbable over a prolonged period of time to counteract the craving for at least about 20 minutes after oral manipulation of the base material commences;
mixing the craving reduction compound with the base material; and
forming the mixture of the base material and oral reduction compound into a unit suitable for being retained in the mouth and thereafter orally manipulated.

44. The method of claim 43, including the step of providing as the base material a gum base.

45. The method of claim 44, including the step of forming the mixture into one of a gum and a lozenge.

46. The method of claim 44, including the step of forming the mixture into a gum.

47. The method of claim 43, including the step of providing as the craving reduction compound nicotine.

48. The method of claim 47, including the step of providing the nicotine in the form of at least one of a nicotine salt and nicotine polacrilex.

49. The method of claim 48, including the step of providing the nicotine in only one form.

50. The method of claim 43, including the step of providing a buffering agent, and mixing the buffering agent into the base material.

51. The method of claim 50, including the step of mixing sufficient buffering agent to elevate the pH of a user's mouth to between about 7.5 and 9.5.

52. The method of claim 51, including the step of providing sufficient buffering agent to elevate the pH for at least about 15 minutes.

53. The method of claim 50, including the step of providing the buffering agent from the group consisting of sodium free buffers.

54. The method of claim 50, including the step of providing the buffering agent from the group consisting of bicarbonate and carbonate buffers.

55. The method of claim 50, including the step of providing the buffering agent from the group consisting of calcium carbonate, potassium citrate, and dipotassium phosphate.

56. The method of claim 50, including the step of mixing from about 30 milligrams to about 70 milligrams of buffering agent per unit.

57. A two-stage active agent delivery system that reduces cravings, comprising:
an orally manipulatable gum base material;
a buffer dispersed within said base material; and
an active ingredient intermixed with said base material and said buffer, said active ingredient cooperating with said buffer upon oral manipulation of the base material for therewith causing release of an initial dose of an active agent achieving a rapid transmucosally absorbable pharmacological effect reducing a craving and releasing a second dose of the active agent achieving a prolonged transmucosally absorbable pharmacological effect reducing the craving.

58. The system of claim 57, wherein said buffer is present in sufficient amount to elevate the pH in a user's mouth to between about 7.5 and 9.5.

59. The system of claim 57, wherein said buffer is present in sufficient amount to elevate the pH in a user's mouth for at least 15 minutes.

60. The system of claim 57, wherein the buffer is selected from the group consisting of bicarbonate and carbonate buffers.

61. The system of claim 57, wherein said buffer is a sodium free buffer.

62. The system of claim 57, wherein said buffer is selected from the group consisting of calcium carbonate, potassium citrate, and dipotassium phosphate.

63. The system of claim 57, wherein there is about 30 to 70 milligrams of buffer dispersed throughout said base material.

64. The system of claim 57, wherein said active ingredient is nicotine.

65. The system of claim 64, wherein said nicotine is selected from the group consisting of nicotine salts and nicotine polacrilex.

66. The system of claim 65, wherein the nicotine is of a single form.

67. The system of claim 65, wherein the nicotine is of at least two forms.

68. The system of claim 65, wherein the initial dose release from about 0.2 to about 0.7 milligrams of nicotine within about 5 minutes.

69. The system of claim 68, wherein the initial dose achieves a concentration of about 2 nanograms of nicotine per milliliter of blood.

70. The system of claim 69, wherein the second dose achieves a concentration of about 10 nanograms of nicotine per milliliter of blood.

71. The system of claim 57, wherein the second dose achieves a concentration in the blood of the active ingredient exceeding the concentration achieved by the initial dose.

72. The system of claim 71, wherein the second dose concentration is maintained for at least about 20 minutes.

73. A two-stage nicotine delivery system that reduces tobacco cravings, comprising:
   an orally manipulatable gum base material;
   a non-sodium buffer dispersed within said gum base material; and
   nicotine evenly distributed throughout said gum base material and intermixed with said buffer, said nicotine cooperating with said buffer upon oral manipulation of the gum base material by a user for therewith causing release of an initial dose of nicotine achieving a rapid transmucosally absorbable pharmacological effect reducing tobacco craving and thereafter releasing a second dose of the nicotine upon subsequent oral manipulation of the gum base material by the user for achieving a prolonged transmucosally absorbable pharmacological effect reducing the tobacco craving.

74. A two stage active ingredient delivery system, comprising:
   a) a base suitable for being received within the oral cavity of a user;
   b) a buffer uniformly distributed throughout said base for being released into the oral cavity of the user for thereby causing the pH within the oral cavity to be elevated; and
   c) an active ingredient uniformly distributed throughout said base so that when the base is placed with the oral cavity at least some of the buffer is released and thereby elevates the pH within the oral cavity and an initial dose of said active ingredient is release sufficient to achieve a rapid transmucosally absorbable pharmacological effect and further release of said active ingredient is sufficient to achieve a prolonged transmucosally absorbable pharmacological effect.

* * * * *